United States Patent [19]

Croucher

[11] Patent Number: 5,520,884
[45] Date of Patent: May 28, 1996

[54] PORTABLE SHAKER FOR USE WITH WATER BATH

[76] Inventor: Michael W. Croucher, 5059 Pine Valley Loop, Smithville, Tex. 78957

[21] Appl. No.: 472,068

[22] Filed: Jun. 7, 1995

Related U.S. Application Data

[63] Continuation of Ser. No. 297,008, Aug. 29, 1994, abandoned, which is a continuation of Ser. No. 260,091, Jun. 15, 1994, abandoned, which is a continuation of Ser. No. 104,250, Aug. 9, 1993, abandoned, which is a continuation of Ser. No. 813,259, Dec. 24, 1991, abandoned.

[51] Int. Cl.$^6$ ..................................... B01L 7/02
[52] U.S. Cl. .................. 422/99; 422/104; 366/240
[58] Field of Search ............. 422/99, 104; 366/237, 366/239, 240; 134/117

[56] References Cited

PUBLICATIONS

Fisher Scientific 1983 catalog pp. 78–81.

*Primary Examiner*—Lyle A. Alexander
*Attorney, Agent, or Firm*—Akin, Gump, Strauss, Hauer & Feld

[57] ABSTRACT

A portable shaker which can be adapted to be attached to a wide variety of water baths. The portable shaker apparatus of the present invention can be removed from one water bath and moved to another water bath to allow the user to avoid the expense of purchasing multiple baths. The preferred embodiment of the invention comprises a removable transport cage assembly which can be inserted into a water bath; means for generating reciprocating motion; means for communicating said reciprocating motion to said support assembly and means for releasably securing said support means to the water bath container. The transport cage used in the preferred embodiment of the invention comprises a frame assembly which is inserted into the water bath and is releasably secured therein. The frame comprises a mounting apparatus which can be adapted to fit a wide variety of water baths. In addition, the frame can be adjusted vertically to accommodate a wide variety of sizes of specimen containers. The means for generating reciprocating motion comprises a cam assembly which is driven by an electric motor.

1 Claim, 4 Drawing Sheets

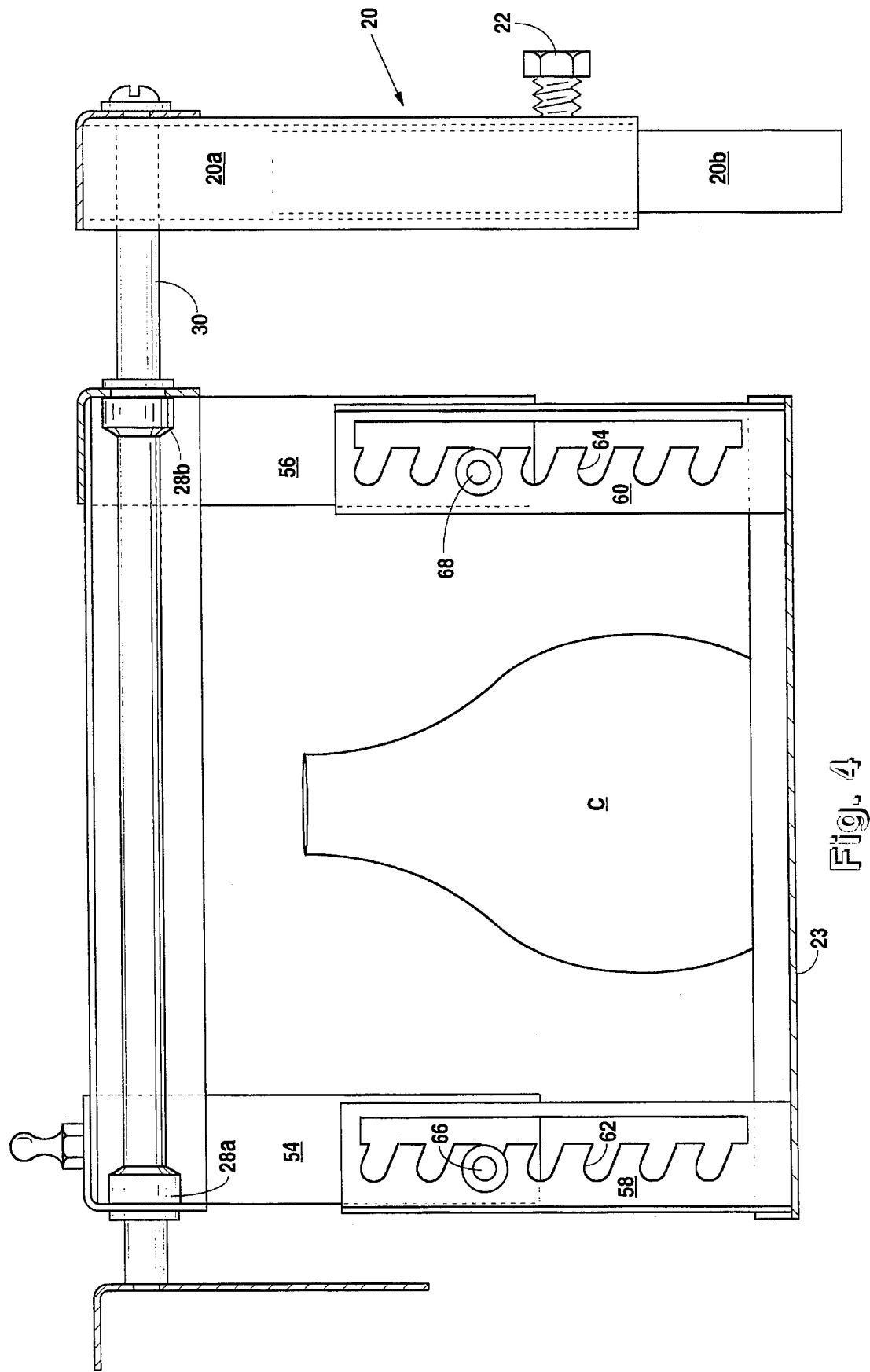

5,520,884

PORTABLE SHAKER FOR USE WITH WATER BATH

This is a continuation of application Ser. No. 08/297,008, filed on Aug. 29, 1994, now abandoned, which is a continuation of pending application Ser. No. 08/260,091 filed on Jun. 15, 1994, now abandoned which is a continuation of abandoned application Ser. No. 08/104,250 filed Aug. 9, 1993, now abandoned, which is a continuation of abandoned application Ser. No. 07/813,259 filed on Dec. 24, 1991 now abandoned.

FIELD OF INVENTION

The present invention relates generally to a water bath shaker apparatus. More specifically, the present invention provides a portable shaker apparatus which can be configured to be used with water baths having a wide variety of dimensions.

BACKGROUND

Laboratory mixers and shaking devices are used in a wide variety of applications related to research and in product fabrication. Most prior art shakers are integral units comprising a water vessel with a oscillating mechanism built into the vessel housing. Test tubes or other containers are placed into a water bath in the vessel and are moved in an oscillatory motion to enhance tile chemical or biological reactions of tile materials or organisms in tile container.

In general, prior art shaker water baths are sufficiently expensive that a typical laboratory cannot afford to have a wide variety of sizes of water baths for each of the possible applications. There is a need, therefore, for a portable shaker apparatus which can be used on a wide variety of water bath vessels. Such a portable shaker apparatus is provided by the present invention, discussed in greater detail below.

SUMMARY OF THE INVENTION

The present invention overcomes the difficulties of the prior art by providing a portable shaker which can be adapted to be attached to a wide variety of water baths. The preferred embodiment of the invention comprises a removable container transport cage which can be inserted into a water bath; means for generating reciprocating motion; means for communicating said reciprocating motion to said transport cage and means for releasably securing said transport cage with respect to the water bath container to allow reciprocating motion therein. In the preferred embodiment, the means for releasably securing the transport cage with respect to the water bath comprises a clamping mechanism for securing a transport cage support structure to the sidewall of the water bath. The means for generating reciprocating motion comprises a cam assembly which is driven by an electric motor. The reciprocating motion is communicated to the transport cage assembly by a mechanical linkage. The transport cage can be adjusted vertically to accommodate a wide variety of sizes of specimen containers. The portable shaker apparatus of the present invention can be removed from one water bath and moved to another water bath to allow the user to avoid the expense of purchasing multiple baths.

BRIEF DESCRIPTION OF THE DRAWINGS

FIG. 4 is cross-sectional view taken along section lines 4—4 of FIG. 1, showing details relating to the container transport cage used in the shaker of the present invention.

DETAILED DESCRIPTION OF THE PREFERRED EMBODIMENT

Figure 1:
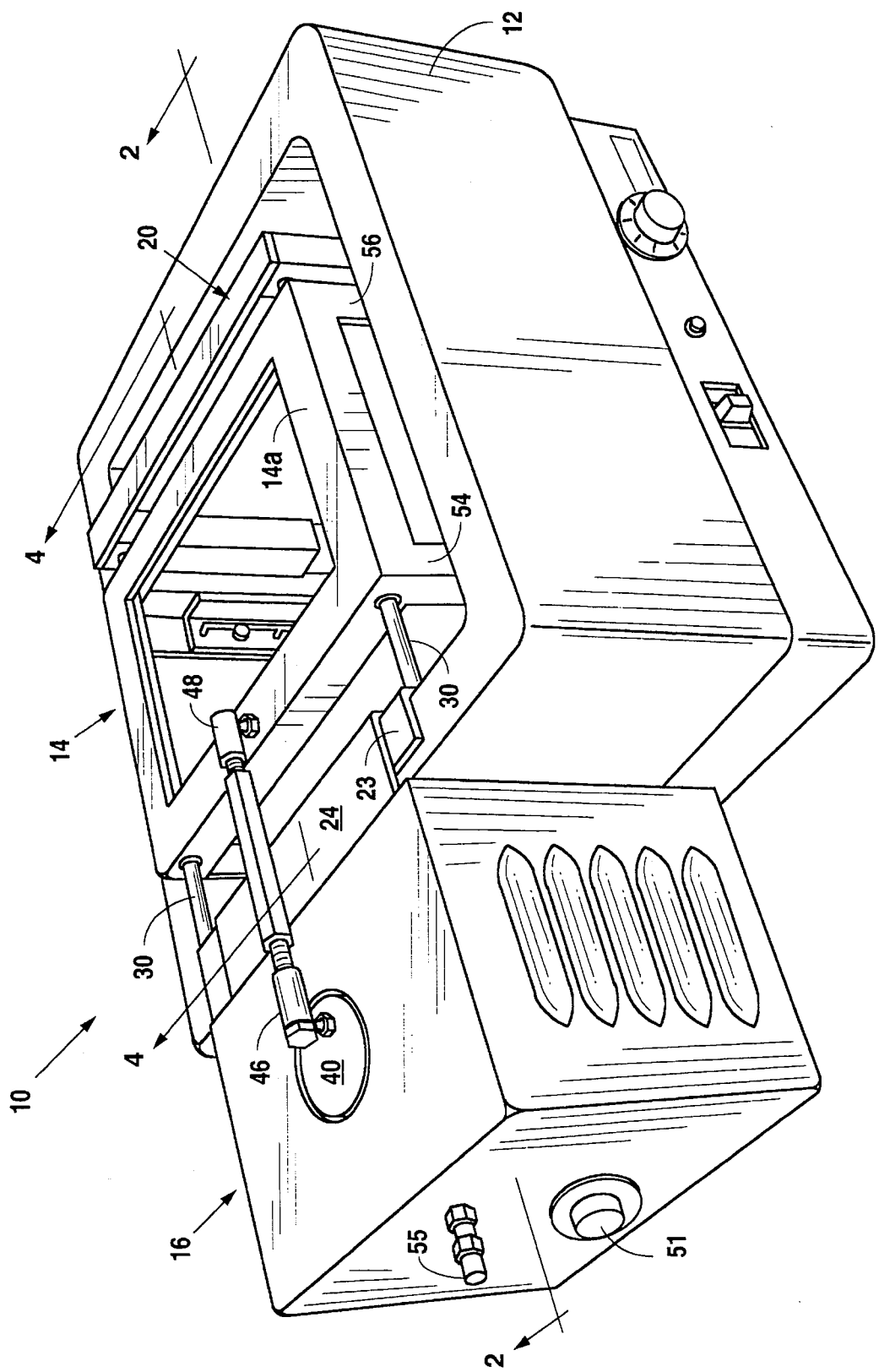
FIG. 1 is a perspective view of the shaker of the present invention attached to a water bath.
Figure 2:
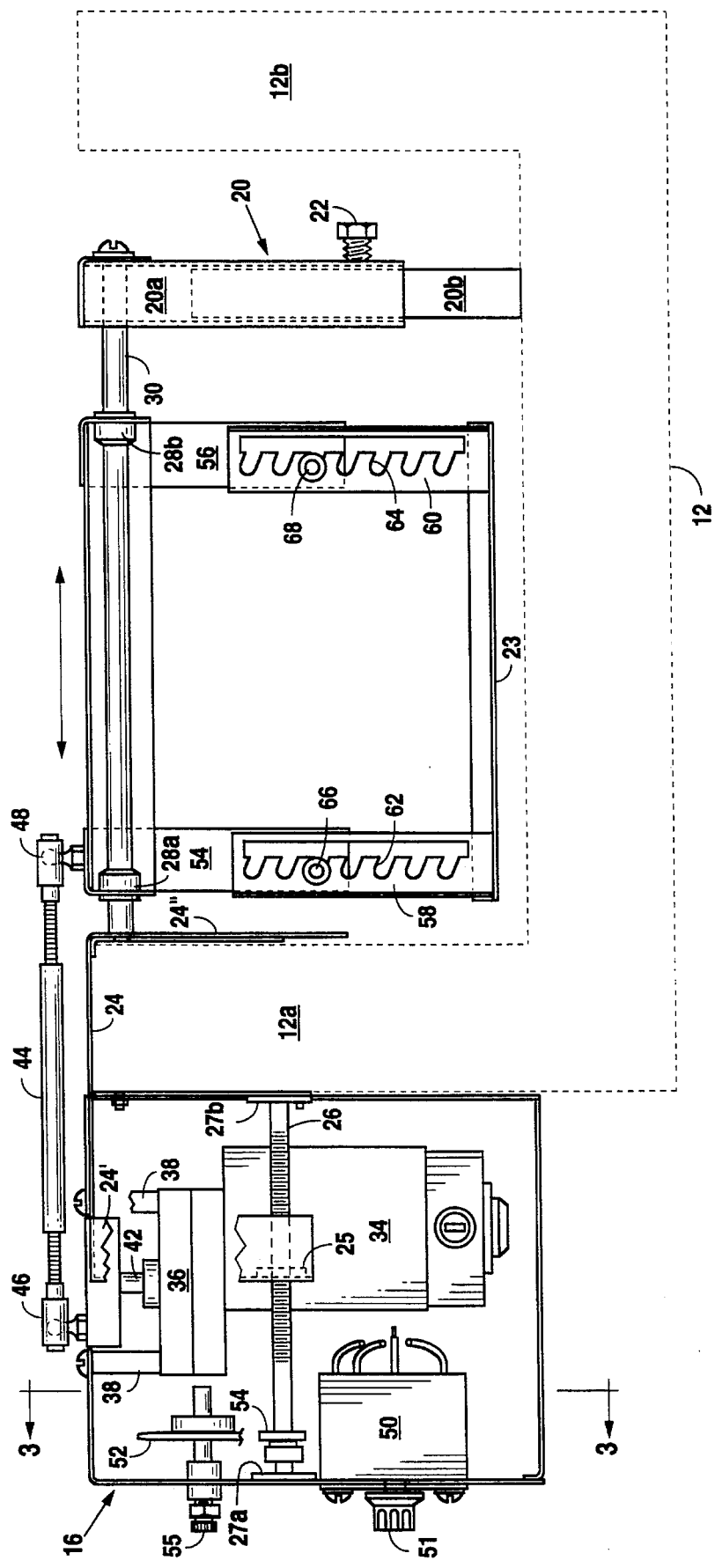
FIG. 2 is a cross-sectional view take along section lines 2—2 of FIG. 1 showing details relating to the internal construction of the shaker of the present invention.

Referring to FIG. 1, the portable water bath shaker 10 of the present invention is shown attached to a water bath housing 12. FIG. 2 is a cross-sectional view taken along section lines 2—2 of FIG. 1 showing details relating to the construction of the portable shaker. FIGS. 1 and 2 will be discussed in conjunction to describe the major elements of the portable shaker of the present invention. Details relating to the means for securing the shaker to the water bath will be discussed in connection with FIG. 3; and details relating the container transport cage Will be discussed in connection with FIG. 4.

Referring to FIG. 1, it can be seen that the portable shaker of the present invention is broadly comprised of a container transport cage 14 and a housing 16 which contains a motor for providing reciprocating motion of the container transport cage and also contains means for releasably securing the shaker to the sidewall of the water bath. The transport cage 14 is a generally cube-shaped assembly. Referring to FIG. 2, it can be seen that one end of the transport cage is supported in the water bath by a support frame comprising upper and lower U-shaped frame members 20a and 20b, respectively. The height of the support frame is determined by securing the legs of the U-shaped members 20a and 20b with an appropriate fastening means such as the bolt 22 shown in FIG. 2. The other end of the transport cage is supported by a bracket 23, seen best in FIG. 1. The bracket 23, which has an L-shaped cross-section, rests on the upper surface of the sidewall 12a of the waterbath. A U-shaped bracket 24 overlies the L-shaped bracket 23 and extends into the housing 16. One side of the U-shaped bracket comprises two legs 24', one of which is shown in the cross-sectional view of FIG. 2. A threaded member 25 in the lower end of each of the legs 24' has a clamp shaft bolt 26 received therethrough. One of the clamp shafts 26 is shown in FIG. 2. The clamp shaft bolt 26 is journaled for rotation in end bearings 27a and 27b. Rotation of the clamp shaft bolts 26 in the threaded members 25 causes the U-shaped bracket 24 to move with respect to the housing 16, thereby causing the leg 24Δ of the U-shaped bracket 24 to come into contact with the inner surface of the sidewall 12a of the water bath.

Each side of the container transport cage 14 comprises a pair of bearings 28a and 28b which are received on rods 30 to allow the cage to slide back and forth in the water bath in a reciprocating motion. The ends of the rods 30 are attached to the support frame 20 and the bracket 23, as seen best in FIG. 1.

The reciprocating motion is provided by a motor 34 contained in the housing 16. A gear assembly 36 is attached to the motor to provide reduction in the number of RPMs of the motor 34. The motor is secured to the housing by a pair of screws 38. An eccentric cam 40 attached to the motor shaft 42 translates the rotational movement of the motor into reciprocating motion via a crankshaft 44 which is attached to ball joints 46 and 48 on the cam 40 and the transport cage, respectively. Operation of the motor is controlled by a controller 50 mounted in the housing 16 as shown in FIG. 2. A control knob 51 allows the user to select the desired motor speed to cause reciprocating movement of the transport cage within the water bath. In the present invention, the rotation of the motor can be adjusted to provide between one revolution per minute and 200 revolutions per minute.

Figure 3:
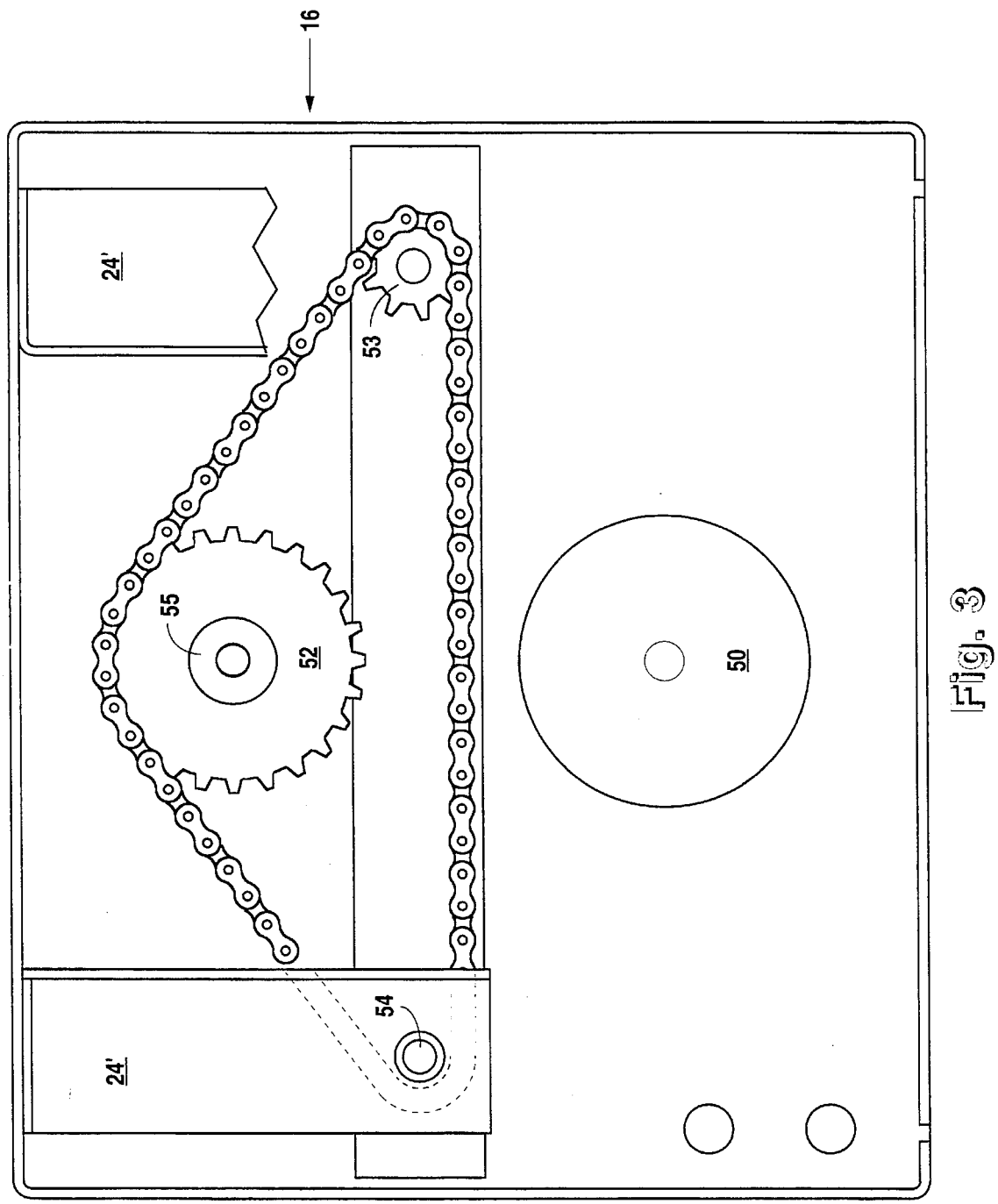
FIG. 3 is s cross-sectional view taken along section lines 3—3 of FIG. 2 showing details relating to the means for securing the shaker to a water bath.

Details relating to the mounting assembly can be seen by referring to FIG. 3. A gear assembly comprising a master gear 52 and clamp shaft gears 53 and 54 is connected by a chain 56. The assembly is operated by turning a control knob 55 which causes the idler gears 53 and 54 to operate clamp shafts 26, as shown in FIG. 2. As discussed above, the clamp shafts 26 are threaded through the threaded members 25 in the lower ends of the legs 24' of the U-shaped bracket 24. As the clamp shafts 26 are rotated, the U-shaped bracket 24 moves with respect to the housing, thereby forcing the housing into contact with the outer surface of the water bath sidewall. In the mounted position, the shaker assembly is clamped on the sidewall 12a of the water bath between the outer surface of the housing 16 and the leg 24Δ of the U-shaped bracket 24. The shaker can be removed from the water bath housing by rotating the control knob 55 to cause the clamp shafts 26 to rotate in a direction that releases the clamping pressure exerted on the water bath sidewall by the housing 16 and the U-shaped bracket 24.

Details relating to the container transport cage 14 can be seen by referring to FIG. 4. As discussed above, the transport cage is a generally cube-shaped frame assembly comprising upper and lower frame members. The upper and lower frame members each comprise a generally rectangular horizontal portion having vertical brackets secured to each corner thereof. The transport cage is formed by securing the vertical brackets of the upper and lower members to form a generally cube-shaped frame assembly. A metal plate or mesh 23 in the lower frame member provides support for containers C carried in the transport cage. In the cross-sectional view of FIG. 4, the brackets 54 and 56 of the upper frame member and the brackets 58 and 60 of the lower frame member are shown in an attached position to form the transport cage. The lower brackets 58 and 60 have a plurality of slots 62 and 64 which can support the lower frame on bolts 66 and 68 of the upper brackets 54 and 56. The position of the lower frame with respect to the upper frame can be adjusted by choosing different slots to support the lower frame. The vertical position of the two cage sections can thereby be adjusted to allow the cage assembly to be expanded or contracted to accommodate a wide variety of sizes of water baths.

Although the method and apparatus of the present apparatus has been described in connection with the preferred embodiment, it is not intended to be limited to the specific form set forth herein, but on the contrary it is intended to cover such alternatives and equivalents as can be reasonably included in the scope of the appended claims.

What is claimed is:

1. An adjustable shaker apparatus for attachment to a housing, comprising:

an adjustable transport cage for holding a container, said transport cage having an upper and lower cage portion, the location of said lower cage portion bring adjustable with respect to said upper portion to accommodate various sized containers;

means for generating reciprocating motion, said motion generating means comprising a motor assembly causing rotational motion of a cam, said rotational motion of said cam being translated into reciprocating motion by a crankshaft assembly, comprising a first joint attached to said transport cage, a second joint attached to said cam, and a crankshaft connected between said first and second joints;

an adjustable transport cage support, said support comprising a frame assembly having an upper frame portion and a lower frame portion, the location of said lower frame portion being adjustable with respect to said upper portion to allow mounting in housings in a variety of sizes, said transport cage support further comprising at least one member connecting said frame assembly upper portion to a clamping means, and said transport cage further comprising a slide rail assembly received on said clamping means to allow the cage to slide with respect to said clamping means in a reciprocating motion;

a motor mounting enclosure; said motor assembly being contained therein, with one face of said enclosure being adjacent an external sidewall of said housing, said clamping means comprising a bracket having a portion thereof on an internal face of said sidewall at a position opposite said housing, said clamping means being operable to cause said bracket and said face of said housing to exert a clamping force on said sidewall of said housing; and wherein the transport cage support and motion generating means are not permanently attached to the housing so that the shaker apparatus may be inserted and removed from the housing as a unit without disassembly.

\* \* \* \* \*